US012291547B2

(12) United States Patent
Giguère et al.

(10) Patent No.: US 12,291,547 B2
(45) Date of Patent: May 6, 2025

(54) SYNTHESIS OF 3-AZIDO-3-DEOXY-D-GALACTOPYRANOSE

(71) Applicant: UNIVERSITÉ LAVAL, Quebec City (CA)

(72) Inventors: Denis Giguère, Saint-Augustin-de-Desmaures (CA); Jacob St-Gelais, Longueuil (CA); Vincent Denavit, Feugarolles (FR)

(73) Assignee: UNIVERSITÉ LAVAL, Quebec (CA)

( * ) Notice: Subject to any disclaimer, the term of this patent is extended or adjusted under 35 U.S.C. 154(b) by 528 days.

(21) Appl. No.: 17/615,724

(22) PCT Filed: Jun. 12, 2020

(86) PCT No.: PCT/CA2020/050814
§ 371 (c)(1),
(2) Date: Dec. 1, 2021

(87) PCT Pub. No.: WO2020/248068
PCT Pub. Date: Dec. 17, 2020

(65) Prior Publication Data
US 2022/0251129 A1    Aug. 11, 2022

Related U.S. Application Data

(60) Provisional application No. 62/861,476, filed on Jun. 14, 2019.

(51) Int. Cl.
C07H 1/00      (2006.01)
C07H 5/04      (2006.01)
C07H 13/08     (2006.01)
C07H 19/056    (2006.01)

(52) U.S. Cl.
CPC ............ *C07H 1/00* (2013.01); *C07H 5/04* (2013.01); *C07H 13/08* (2013.01); *C07H 19/056* (2013.01)

(58) Field of Classification Search
None
See application file for complete search history.

(56) References Cited

FOREIGN PATENT DOCUMENTS

WO    WO 2014/067986 A1    5/2014
WO    WO 2016/120403 A1    8/2016

OTHER PUBLICATIONS

St-Gelais et al., Organic Biomolecular Chemistry, vol. 18, May 7, 2020, pp. 3903-3907. (Year: 2020).*
International Search Report and Written Opinion for PCT International Patent Application No. PCT/CA2020/050814, mailed Aug. 24, 2020.
International Preliminary Report on Patentability for PCT International Patent Application No. PCT/CA2020/050814, mailed Dec. 14, 2021.
Wei et al., "Highly efficient and versatile synthesis of some important precursors from 1,6-Anhydrous-β-D-glucopyranose as a Green Starting Material", Chinese Journal of Chemistry, Aug. 2009, 27(8): 1589-1592.

* cited by examiner

*Primary Examiner* — Traviss C McIntosh, III
(74) *Attorney, Agent, or Firm* — Christian Cawthorn; NORTON ROSE FULBRIGHT CANADA LLP

(57) ABSTRACT

The present application provides a synthetic method for production of 3-azido-3-deoxy-D-galactopyranose. Also provided are methods of using the 3-azido-3-deoxy-D-galactopyranose in the manufacture of galactoside galectin antagonists, such as TD139 (GB0139), GB1107, GB2064, and GB1211.

19 Claims, No Drawings

SYNTHESIS OF 3-AZIDO-3-DEOXY-D-GALACTOPYRANOSE

CROSS-REFERENCE TO RELATED APPLICATIONS

The present application is a 35 U.S.C. §371 filing of International Patent Application No. PCT/CA2020/050814, filed Jun. 12, 2020, which claims priority to U.S. Provisional Patent Application No. 62/861,476, filed Jun. 14, 2019, which are incorporated herein in their entirety.

FIELD OF THE INVENTION

The present application pertains to the field of chemical synthesis. More particularly, the present application relates to methods for the synthesis of a 3-azido-3-deoxy-D-galactopyranose and the use of this compound in the manufacture of galectin inhibitors.

INTRODUCTION

Galectins are proteins that bind to β-galactoside residues and their natural ligands are any glycoconjugate having a non-reducing galactopyranoside terminus.[1] Galectins have the ability to regulate numerous biological process, including neoplastic transformation, tumor cell survival processes, angiogenesis, and tumor metastasis.[2] Over the years, the scientific community has directed efforts for the exploration of a myriad of structural combinations, in the quest for the synthesis of potent and optimized galectin inhibitors.[3] There are currently numerous clinical trials involving galectin antagonists.[4]

TD139 (also known as GB0139), or compound 1, is a galectin antagonist showing promise in clinical trials.

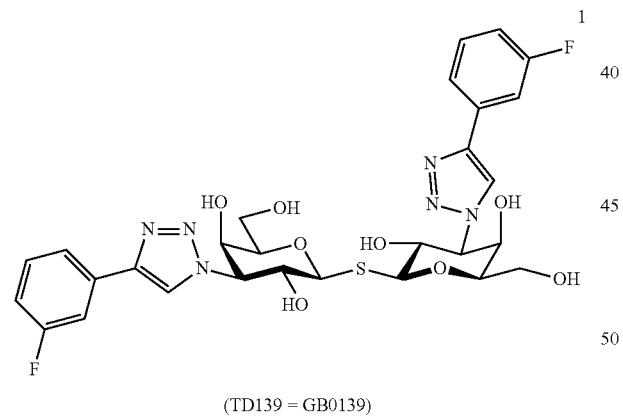

(TD139 = GB0139)

In particular, compound 1 is a thiodigalactoside galectin-3 inhibitor, currently being clinically evaluated for the treatment of idiopathic pulmonary fibrosis.[5] Compound 1 showed a $K_d$ of 14 nM to galectin-3, as determined using a competitive fluorescence anisotropy assay. Compound 1 is a 3,3'-bis-(4-aryltriazol-1-yl) thiodigalactoside that is synthetically accessible from dimerization of a 3-azido-3-deoxy-galactopyranoside.[6]

Two distinct approaches have been reported regarding the preparation of 1,2,4,6-tetra-O-acetyl-3-azido-3-deoxy-D-galactopyranose. The first approach involves a nucleophilic displacement of a gulofuranose triflate derivative.[7] This approach makes use of an expensive starting material, namely gulofuranose, which can be accessed from glucose in a long 6-step protocol.[8] The second approach involves introduction of the 3-azido functionality by double inversions at C-3 of 4,6-βO-benzylidene-β-D-galactopyranosides with triflate intermediates.[9] Because of the instability of the triflate intermediates, this method was later improved by using more stable imidazylate and tosylate intermediates.[10]

A need remains for a more convenient preparation of 3-azido-3-deoxy-galactose to facilitate cost effective large scale synthesis of thiodigalactoside galectin inhibitors, such as compound 1.

The above information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present application is to provide a method for synthesis of 3-azido-3-deoxy-D-galactopyranose, and a method of production of galactoside galectin inhibitors from the 3-azido-3-deoxy-D-galactopyranose synthesized thereby.

In accordance with an aspect of the present application, there is provided method for synthesizing a 3-azido-3-deoxy-D-galactopyranose of formula IV

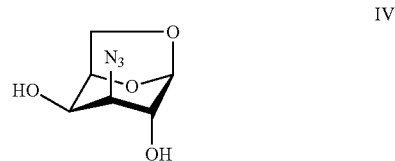 [SMILES: [N-]=[N+]=N[C@H]1C(O)[C@@H]2OCC(O2)[C@@H]1O]

said method comprising:
(a) a one step or two-step epoxidation of a compound of formula II to form a compound of formula III

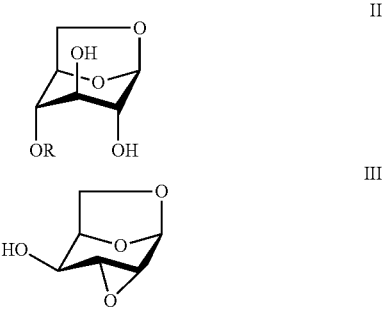

where R is an activating group, such as, but not limited to sulfonyl, trifluoromethanesulfonyl, or imidazole-1-sulfonyl;
(b) ring opening of the epoxide of the compound of formula III with an organic or inorganic azide to produce the compound of formula IV.

Optionally, prior to step (a), the method above additionally comprises treating levoglucosan with an activating agent to produce the compound of formula II.

The method of synthesizing the compound of formula IV can be incorporated into a method for manufacture of a galactoside galectin inhibitor.

In accordance with another aspect of the present application, there is provided a method for synthesis of a compound having the structure of formula Ia or Ib,

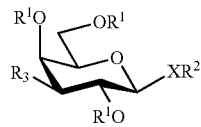

Ia

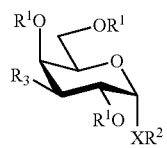

Ib wherein:
each $R^1$ is independently H or a protecting group, such as acetyl, benzyl (Bn), p-methoxybenzyl (PMB), substituted benzyl, trimethylsilyl (TMS), t-butyldimethylsilyl (TBS), or t-butyldiphenylsilyl (TBDPS);
$R^2$ is alkyl, substituted alkyl, aryl, substituted aryl, heteroaryl, substituted heteroaryl, or a substituted α- or β-D-galactopyranosyl;
$R^3$ is a substituted or unsubstituted nitrogen-containing functional group, such as azide, amine, amide, sulfonamide, carbamate or substituted nitrogen-based heterocycle, such as triazole, or substituted triazole (e.g., mono-fluorophenyl triazole, di-fluorophenyl triazole, or trifluorophenyl triazole); and
X is O, S, or N,
said method comprising:
(a) epoxidation of a compound of formula II to form a compound of formula III

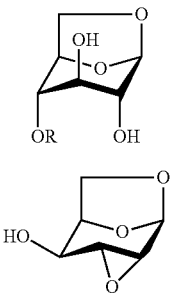

where R is an activating group;
(b) ring opening the epoxide of the compound of formula III with an inorganic or organic azide to produce the compound of formula IV

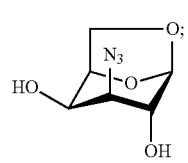

(c) protecting the alcohol groups of the compound of formula IV and subsequently treating the protected compound with an activator to break the 1,6-anhydro bridge, or treating the compound of formula IV with an activator to break the 1,6-anhydro bridge and simultaneously protecting the alcohol groups;
(d) performing one or more nucleophilic substitutions to introduce $R^2X$ at C1 of the galactopyranose ring of the product of step (c), after or simultaneously with breaking the 1,6-anhydro bridge, to form a compound of formula Ia' or Ib'

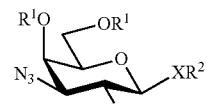

Ia'

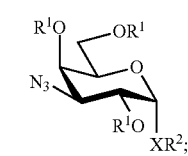

Ib';

and, optionally
(e) treating the compound of formula Ia' or Ib' to replace the azide with another nitrogen-containing functional group.

In accordance with one embodiment, the above method is used to synthesize a monosaccharide derivative as a galectin inhibitor. In other embodiments, the above method is used to synthesize a disaccharide derivative as a galectin inhibitor. In one example of this embodiment, the method additionally comprises, prior to step (e), performing a base-promoted substitution of a galactopyranosyl-1-halide with the compond formula Va to form a compound of Ia in which $R^2$ is a β-D-galactopyranosyl.

In accordance with certain embodiments, the methods described herein are used to manufacture a galectin inhibitor selected from the group consisting of:

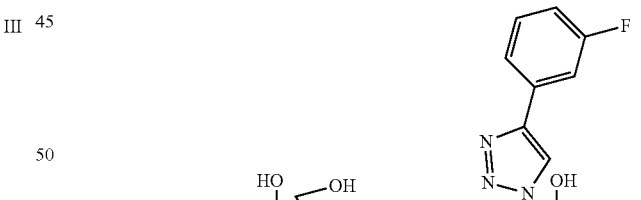

-continued

GB1107

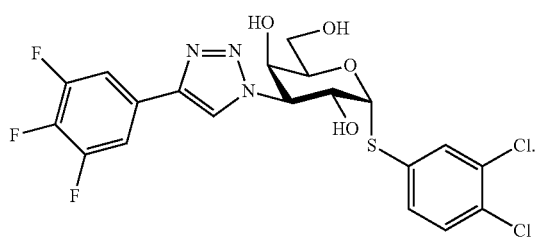

DETAILED DESCRIPTION

Definitions

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s), and/or ingredient(s), as appropriate.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from the exemplary group including, but not limited to, halo, hydroxy, alkoxy, oxo, alkanoyl, aryloxy, alkanoyloxy, amino, alkylamino, arylamino, arylalkylamino, disubstituted amines (e.g., in which the two amino substituents are selected from the exemplary group including, but not limited to, alkyl, aryl, or arylakyl), alkanylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamido (e.g. —SO$_2$NH$_2$), substituted sulfonamide, nitro, cyano, carboxy, carbamyl (e.g. —CONH2), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like. In particular embodiments, the galectin inhibitor compounds made using the process of the present application include functional groups that include one or more fluoro substituent.

As used herein, the term "alkyl," unless otherwise specified, is intended to have its accustomed meaning of a straight, branched or cyclic chain hydrocarbon, for example, methyl, ethyl, n-propyl, isopropyl, n-butyl, sec-butyl, t-butyl, n-pentyl, sec-pentyl, t-pentyl, neopentyl, and the like. In some embodiments, alkyl groups have from 1 to 20 carbon atoms or from 1 to 10 carbon atoms. As used herein, the term "substituted alkyl" refers to an alkyl that includes one or more substitution as defined above. In particular examples, a "substituted alkyl" is any fluorinated, non-aromatic, hydrocarbon.

As used herein, the term "aryl," unless otherwise specified, is intended to mean an aromatic hydrocarbon system for example phenyl, naphthyl, phenanthrenyl, anthracenyl, pyrenyl, and the like. In some embodiments, aryl groups have from 6 to 10 carbon atoms. As used herein, the term "substituted aryl" refers to an aryl that includes one or more substitution as defined above. In particular examples, a "substituted aryl" is any fluorinated aromatic hydrocarbon.

As used herein, the term "heteroaryl," unless otherwise specified, is intended to mean an aryl group that contains one or more ring hetero (i.e., non-carbon) atoms, which are preferably O, N, or S. In some embodiments, heteroaryl groups are monocyclic or bicyclic, and have up to four ring heteroatoms. Examples of some heteroaryl groups include radicals derived from pyrrole, pyrazole, imidazole, triazoles, tetrazole, pyridine, pyrazine, pyndazine, pyrimidine, triazines, quinolines, indoles, benzimidazoles, and the like. As used herein, the term "substituted heteroaryl" refers to heteroaryl that includes one or more substitution as defined above. In particular examples, a "substituted heteroaryl" is any fluorinated aryl group that contains one or more heteroring.

The present application provides a synthetic method for production of a 3-azido-3-deoxy-D-galactopyranose, such as 1,2,4,6-tetra-O-acetyl-3-azido-3-deoxy-D-galactopyranose, which is a compound useful in the production of galactoside galectin inhibitors (for example TD139 (GB0139)).

Also provided herein are methods for synthesizing galactoside galectin inhibitors using a 3-azido-3-deoxy-D-galactopyranose, such as 1,2,4,6-tetra-O-acetyl-3-azido-3-deoxy-D-galactopyranose, as a starting material or an early intermediate.

The present synthetic methods are amenable to large scale production, starting from an inexpensive starting material, and offer a practical alternative to known reported methods for production of galectin inhibitors, including 1,2,4,6-tetra-O-acetyl-3-azido-3-deoxy-D-galactopyranose.[7,8,9]

In particular embodiments, the synthetic method for synthesizing a 3-azido-3-deoxy-D-galactopyranose of formula IV

IV

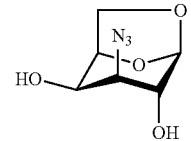

comprises:
(a) epoxidation of a compound of formula II to form a compound of formula III

II

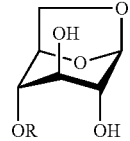

-continued

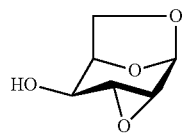

III where R is an activating group; and (b) ring opening of the epoxide of the compound of formula III with an organic or inorganic azide to produce the compound of formula IV.

The compound of formula IV is useful in the preparation of mono- and di-galactoside galectin inhibitors, such as, but not limited to those described in WO 2005/113568, WO 2005/113569, WO 2010/126435, WO 2014/067986, WO 2020/104335, WO 2019/13797, WO 2018/011094, WO 2018/011093, WO 2016/0804, WO 2019/075045, and WO 2020/078808, which are incorporated by reference in their entirety.

In specific embodiments, the method of the present invention is used to manufacture one of the following galactoside galectin inibitors:

| Name | Structure | Reference |
|---|---|---|
| Di-amido-thiodigalactoside | 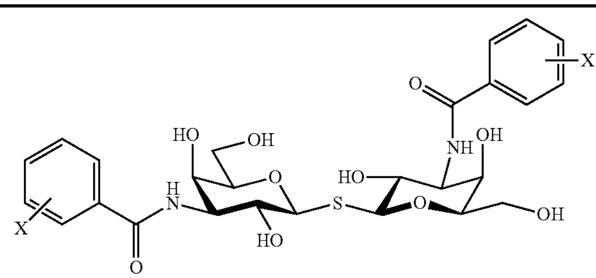 | Delaine, T.; Cumpstey, I.; Ingrassia, L.; Le Mercier, M.; Okechukwu, P.; Leffler, H.; Kiss, R.; Nilsson, U. J. J. Med. Chem. 2008, 51, 8109-8114 |
| GB1107 | 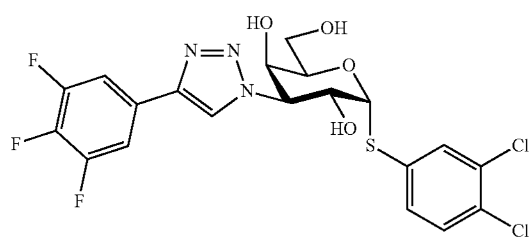 | Vuong, L et al. Cancer Res. 2019, 79, 1480-1492 |
| GB1211 | Developed by Galecto Manufactured by Falecto Biotech, Currently in clinical phase 1 | NCT03809052 |
| GB2064 | Manufactured by Galecto Biotech and currently in preclinical development | |

The present application further provides a synthetic method for production of a galectin inhibitor, or a protected galectin inhibitor, of the general formula I from the compound of formula IV

I wherein:

each $R^1$ is independently H or a protecting group, such as acetyl, substituted ester, benzyl, p-methoxybenzyl (PMB), substituted benzyl, trimethylsilyl (TMS), t-butyldimethylsilyl (TBS), or t-butyldiphenylsilyl (TBDPS);

$R^2$ is alkyl, substituted alkyl, aryl, substituted aryl, heteroaryl, substituted heteroaryl, or a substituted β-D-galactopyranosyl;

$R^3$ is a substituted or unsubstituted nitrogen-containing functional group, such as azide, amine, amide, sulfonamide, carbamate or substituted nitrogen-based heterocycle, such as triazole, or substituted triazole (e.g., mono-fluorophenyl triazole, di-fluorophenyl triazole, or trifluorophenyl triazole); and X is O, S, or N.

In particular embodiments, the synthetic method for production of galectin inhibitors of the general formula I can be summarized as shown in the scheme below:

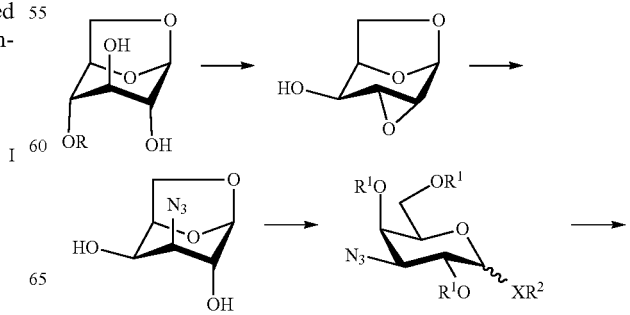

-continued

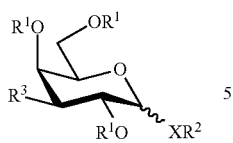

where R¹, R² and R³ are as defined above.

In accordance with certain embodiments, there is provided a synthetic method for producing a compound having the structure of formula Ia or Ib,

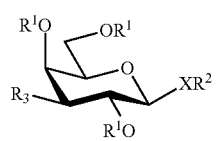

Ia

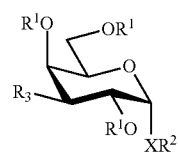

Ib wherein:
- each R¹ is independently H or a protecting group, such as acetyl, substituted ester, benzyl (Bn), p-methoxybenzyl (PMB), substituted benzyl, trimethylsilyl (TMS), t-butyldimethylsilyl (TBS), or t-butyldiphenylsilyl (TBDPS);
- R² is alkyl, substituted alkyl, aryl, substituted aryl, heteroaryl, substituted heteroaryl, or a substituted α- or β-D-galactopyranosyl;
- R³ is a substituted or unsubstituted nitrogen-containing functional group, such as azide, amine, amide, sulfonamide, carbamate or substituted nitrogen-based heterocycle, such as triazole, or substituted triazole (e.g., mono-fluorophenyl triazole, di-fluorophenyl triazole, or trifluorophenyl triazole); and
- X is O, S, or N, said method comprising:
(a) epoxidation of a compound of formula II to form a compound of formula III

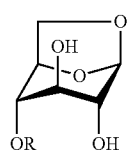

II

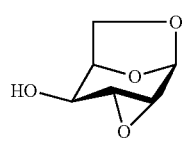

III where R is an activating group;

(b) ring opening of the epoxide of the compound of formula III with an inorganic or organic azide to produce the compound of formula IV

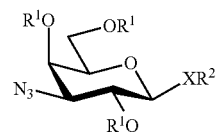

IV (c) protecting the alcohol groups of the compound of formula IV and subsequently treating the protected compound with an activator to break the 1,6-anhydro bridge, or treating the compound of formula IV with an activator to break the 1,6-anhydro bridge and simultaneously protecting the alcohol groups;

(d) performing one or more nucleophilic substitutions to introduce R²X at C1 of the galactopyranose ring of the product of step (c), after or simultaneously with breaking the 1,6-anhydro bridge, to form a compound of formula Ia' or Ib'

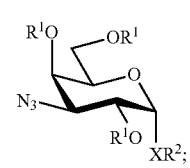

Ia'

Ib' and, optionally
(e) treating the compound of formula Ia' or Ib' to replace the azide with another nitrogen-containing functional group.

Functionalization with a nitrogen-containing functional group at the C3 position galactopyranoside ring can be achieved using standard synthetic techniques. The following schemes illustrate specific embodiments of the use of such techniques in the synthesis of galactoside galectin inhibitors comprising a substituted triazole, a primary amine, a secondary amine, an amide or a sulfonamide at the C3 position.

General

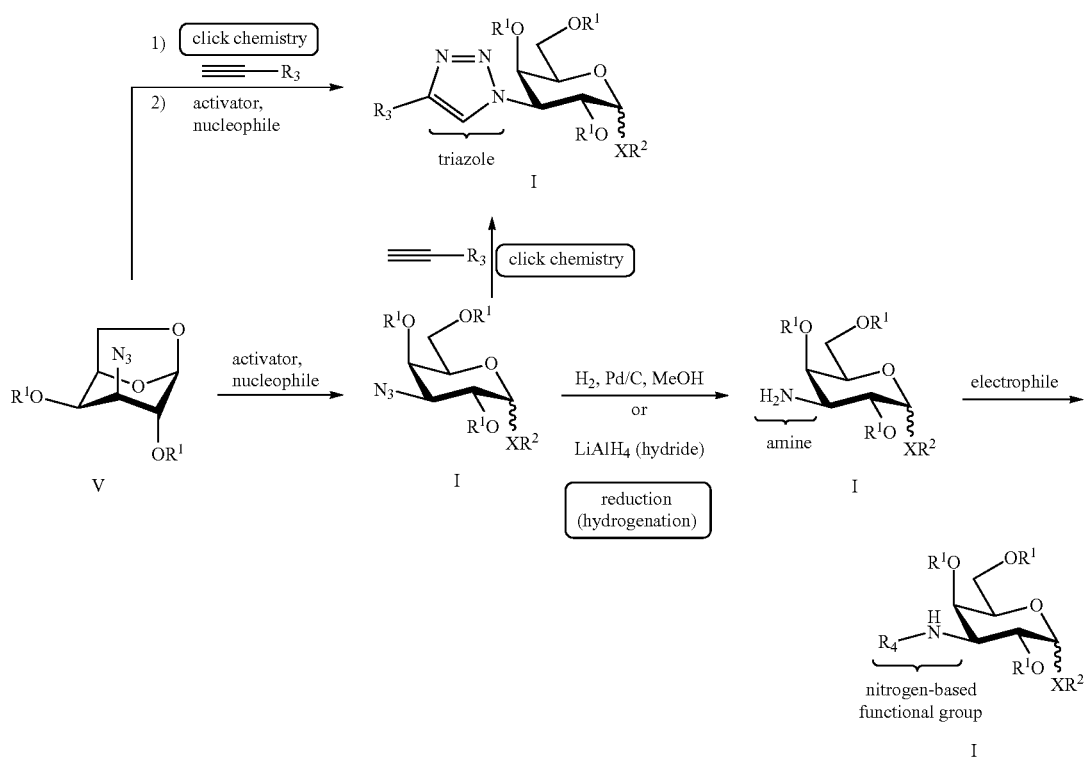

Specific Examples of Nitrogen-Based Functional Groups

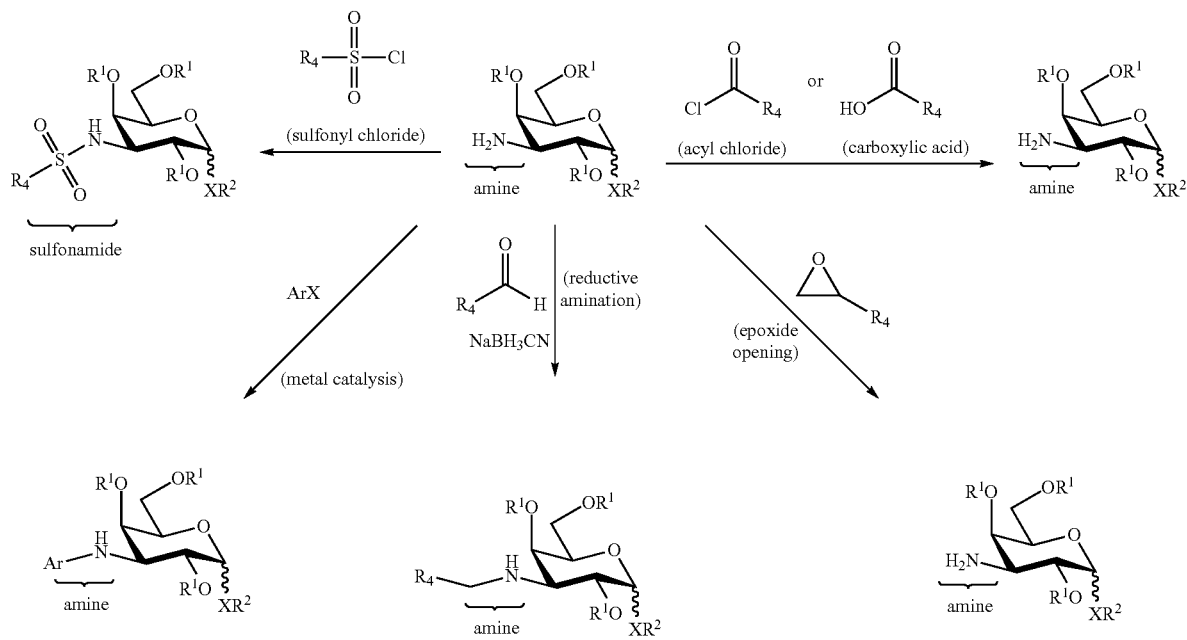

As an example, an efficient synthesis of TD139 (GB0139) 1 from levoglucosan is described herein. This synthesis includes what is currently the shortest publicly known route to 3-azido-3-deoxy-galactopyranose, a crucial intermediate for the preparation of bis-(2,4,6-tri-O-acetyl-3-azido-β-D-galactopyranosyl)-sulfane. Finally, this synthetic method for the production of 3-azido-3-deoxy-galactopyranose allows the preparation of galactose derivatives functionalized at C-3 and, therefore, can provide useful options for the synthesis of other selective and efficient galectin inhibitors.

Levoglucosan was selected as the starting material since the 1,6-anhydro core avoids the preliminary protection of O-6 and anomeric positions. Use of levoglucosan as the starting material has now been found to lead to scalable 3-azido-3-deoxy-galactose derivatives via simple synthetic protocols.

As set out in the synthetic scheme below (Scheme 1), the method of the present application comprises preliminary activation of O-4 of levoglucosan. In the non-limiting example shown in Scheme 1, activation is achieved using a sulfonyl group to form 1,6-anhydro-4-O-p-tolylsulfonyl-β-D-glucopyranose 2.

Scheme 1

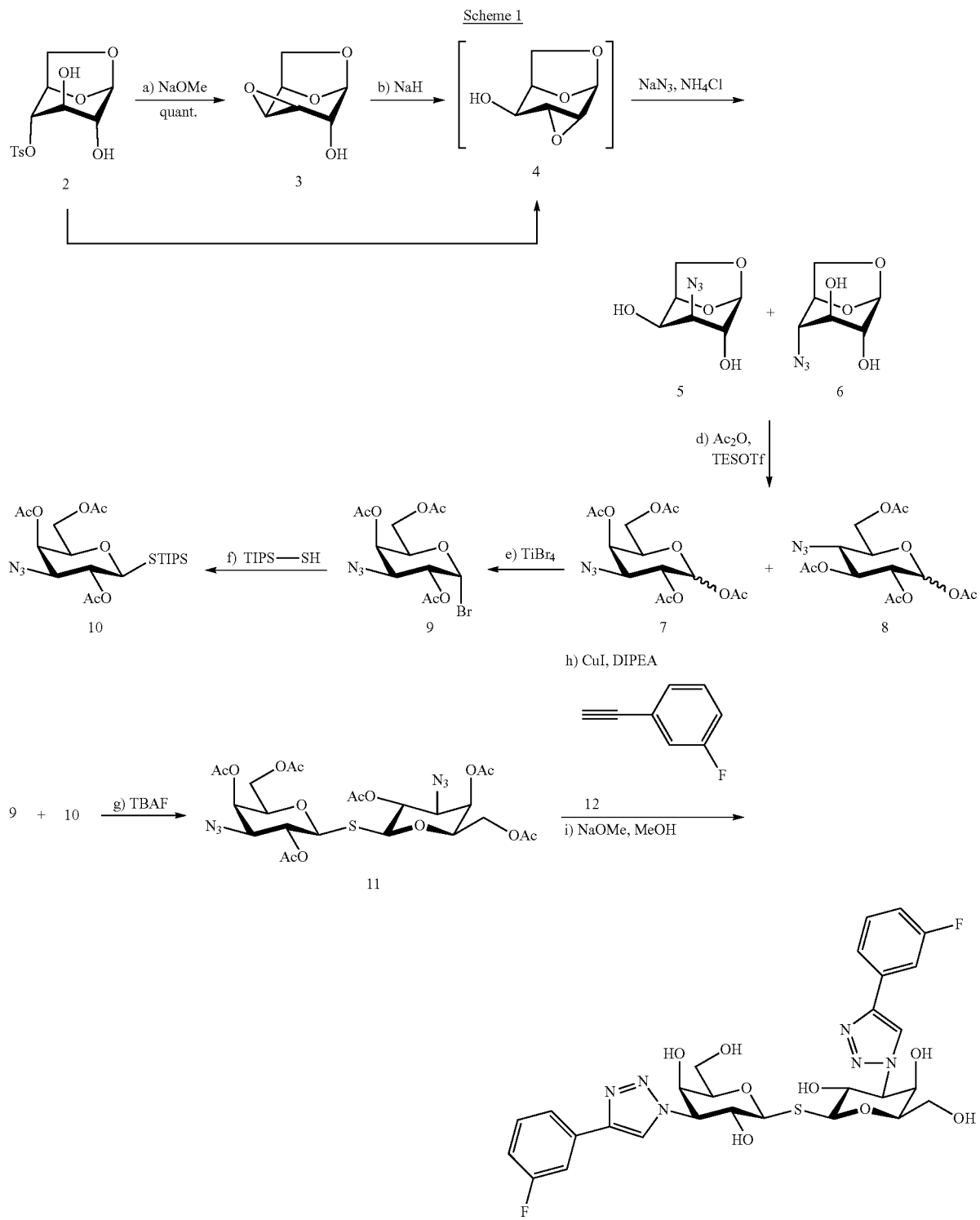

1: TD139

In the example shown in Scheme 1, the activated (e.g., sulfonylated) levoglucosan is then treated to form an epoxide, 1,6:3,4-dianhydro-β-D-galactopyranose 3, typically in quantitative yield. Treatment of compound 3 with a base, for example sodium hydride, induces a Payne rearrangement, allowing an equilibrium between compounds 3 and 4. Next, opening of the epoxide with an inorganic azide, for example sodium azide, yields an inseparable mixture of 1,6-anhydro-3-azido-3-deoxy-β-D-galactopyranose 5 and 1,6-anhydro-4-azido-4-deoxy-β-D-glucopyranose 6 (5:6, 9:1). Using the experimental details set out in Example 1, this step can produce compounds 5 and 6 in 90% yield.

In an alternative embodiment, compound 2 is treated with a base, for example sodium hydroxide, which promotes epoxide formation and Payne rearrangement. The crude mixture from that reaction is then subjected to treatment with an inorganic azide, for example sodium azide, providing compounds 5 and 6. Using the experimental details set out in Example 1, this step can produce compounds 5 and 6 in 81% yield (5:6, 4:1).

Production of the 3-azido-3-deoxy-β-D-galactopyranose derivative from levoglucosan in high yield means that the above synthetic method can be incorporated into an overall synthetic approach for cost effective manufacture of galactin inhibitors, such as TD139 1.

Accordingly, another embodiment of the present application provides a method for the production of TD 139 1 from 3-azido-3-deoxy-β-D-galactopyranose derivative 5. One example of this embodiment proceeds as follows (as depicted in Scheme 1 above). Acetolysis of compounds 5 and 6 under acidic conditions (TESOTf, Ac₂O) furnishes a separable mixture of known 3-azido-3-deoxy-galactose 7 and 4-azido-4-deoxy-glucose 8, for example in 96% yield. Next, the anomeric position can be functionalized via a glycosyl halide. For example, the α-galactosyl bromide 9 can be slowly generated using TiBr₄ from intermediate 7. Then, a base-promoted SN₂ substitution of galactosyl bromide 9 with TIPS-SH affords tri-isopropylsilylthio-galactoside 10. The dimeric nature of the thiodigalactoside core was achieved by treating compounds 9 and 10 with a fluoride source, for example, tetrabutylammonium fluoride (TBAF) to generate bis-(2,4,6-tri-O-acetyl-3-azido-3-deoxy-P-D-galactopyranosyl)-sulfane 11. Finally, triazole installation with a known alkyne precedes global deprotection, allowing the preparation of TD139 1 in 2 steps.

Although the above description refers to specific reagents, it should be appreciated that alternative reagents can be used at certain steps along the synthetic route.

Other embodiments provide a method for production of galectin inhibitors from levoglucosan as a starting material. As described above, this method comprises the steps of preliminary activation of O-4 of levoglucosan, for example, with a sulfonyl group to form 1,6-anhydro-4-O-p-tolylsulfonyl-β-D-glucopyranose 2. The activated levoglucosan is then epoxidated. The epoxide is ring-opened using an organic or inorganic azide to produce 1,6-anhydro-3-azido-3-deoxy-β-D-galactopyranose 5. Protection of the alcohol groups of compound 5, using a suitable protecting group (e.g., acetyl, benzyl, p-methoxybenzyl (PMB), trimethylsilyl (TMS), t-butyldimethylsilyl (TBS), t-butyldiphenylsilyl (TBDPS)) affords 1,6-anhydro-3-azido-3-deoxy-β-D-galactopyranose derivatives 20.

Scheme 2 summarizes one embodiment of a method for functionalization of 1,6-anhydro-β-D-galactopyranose derivatives 20, in which a nucleophile and a proper activator (e.g., TMSOTf, TESOTf, SnCl₄, BF₃·OEt₂, ZnI₂, TiBr₄, HBr, AcOH, TsOH, TFA, TfOH or any Bronsted or Lewis acid) are used together to break the 1,6-anhydro bridge and produce galectin inhibitor compounds of general formula 21.

Scheme 2

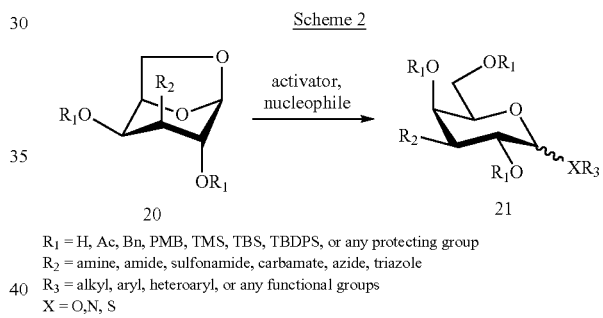

$R_1$ = H, Ac, Bn, PMB, TMS, TBS, TBDPS, or any protecting group
$R_2$ = amine, amide, sulfonamide, carbamate, azide, triazole
$R_3$ = alkyl, aryl, heteroaryl, or any functional groups
X = O, N, S To gain a better understanding of the invention described herein, the following examples are set forth. It should be understood that these examples are for illustrative purposes only. Therefore, they should not limit the scope of this invention in any way.

EXAMPLES

Example 1: Synthesis of TD139 (GB0139; 1) from Levoglucosan

Scheme 1a: Synthesis of TD139 (GB0139) 1 from 1, 6-anhydro-4-O-p-tolylsulfonyl-β-D-glucopyranose 2.

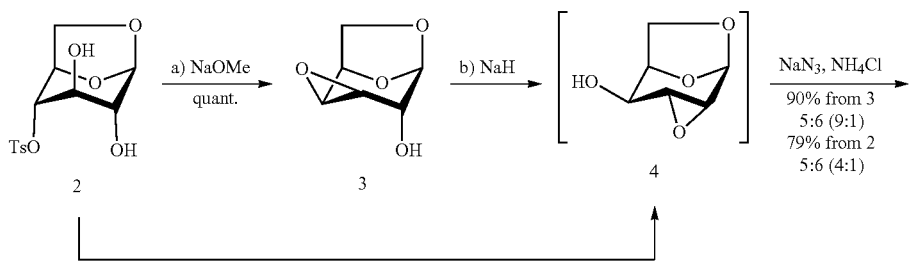

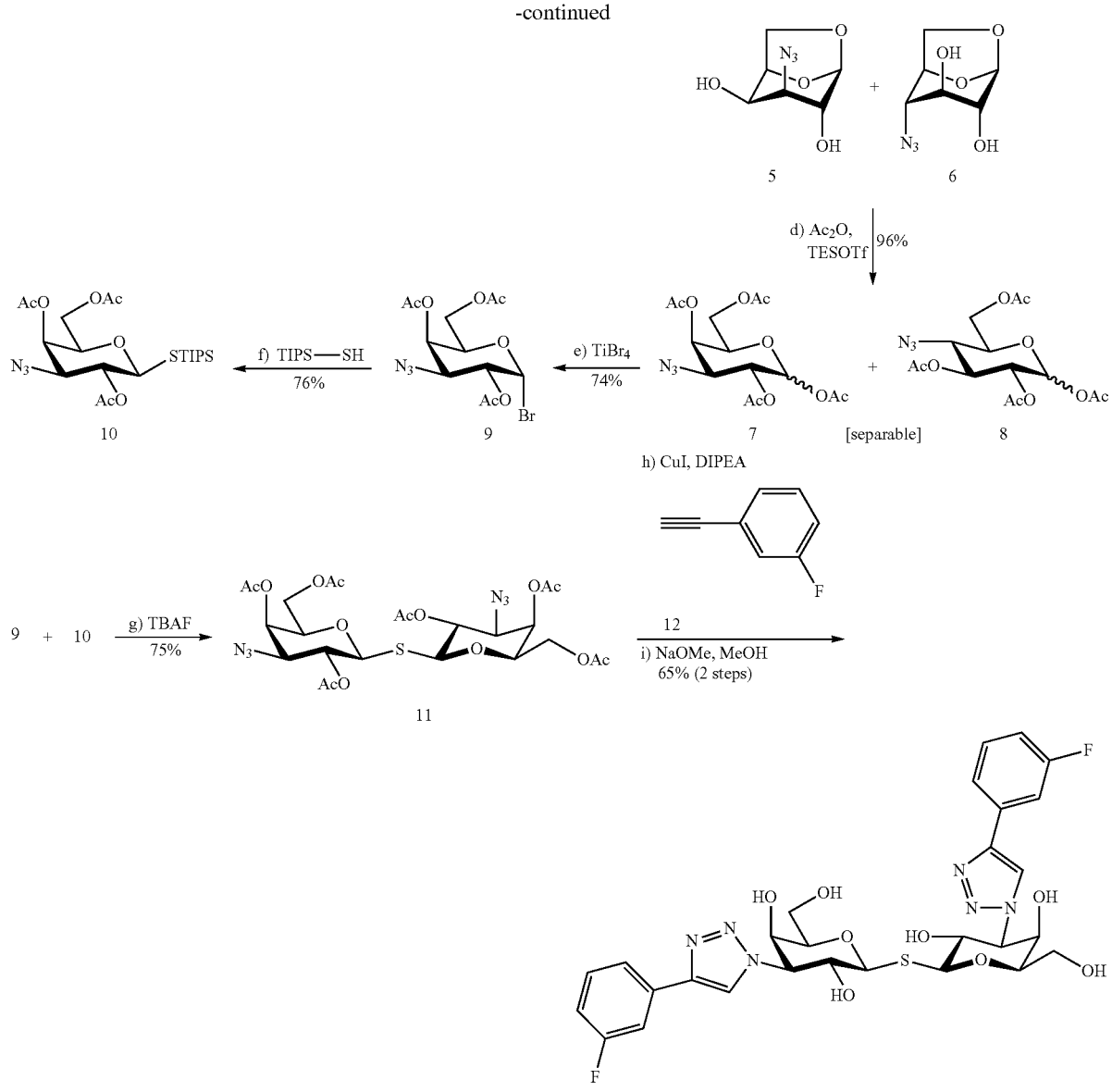

Reagents and conditions: a) NaOMe (1 equiv), MeOH, room temperatue (rt), quant; b) NaH (2 equiv), DMF, rt, 6 h, then NaN₃ (10 equiv), NH₄Cl (5 equiv), 120° C., 18 h, 90% (5:6, 9:1); c) 1M NaOH, H₂O, rt, 3 h, then NaN₃ (10 equiv), NH₄Cl (5 equiv), 100° C., 24 h, 79% (5:6, 4:1); d) Ac₂O, TESOTf (cat.), 0° C, 30 min, 96%; e) TiBr₄ (2 equiv), CH₂Cl₂/EtOAc (10:1), 0° C. to rt, 36 h, 74%; f) K₂CO₃ (3 equiv), HSTIPS (2 equiv), MeCN, rt, 3 h, 76%; g) TBAF (1.5 equiv), MeCN, rt, 0.25 h, 75%; h) 12 (4 equiv), CuI (0.5 equiv), DIPEA (2 equiv), 50° C., 24 h; i) NaOMe, CH₂Cl₂/MeOH (1:4), rt, 18 h, 65% (over 2 steps). Ac₂O = acetic anhydride, DIPEA = N,N-diisopropylethylamine DMF = N,N-dimethylformamide, TBAF = tetrabutylammonium fluoride, TIPS = triisopropylsilyl, TESOTf = triethylsilyl trifluoromethanesulfonate, TsCl = 4-toluenesulfonyl chloride.

General Method

All reactions were carried out under an argon atmosphere with dry solvents under anhydrous conditions, unless otherwise noted. $CH_2Cl_2$, THF, and $CH_3CN$ were purified using a Vacuum Atmospheres Inc. solvent purification system. Yields refer to chromatographically and spectroscopically (¹H NMR) homogeneous materials, unless otherwise stated. Reagents were purchased at the highest commercial quality available and used without further purification, unless otherwise stated. Reactions were monitored by thin-layer chromatography (TLC) carried out on 0.25 mm E. Merck silica gel plates (60F-254) using UV light as visualizing agent and charring with a solution of 3 g of phenol and 5 mL of $H_2SO_4$ in 95 mL of EtOH, followed by heating with a heatgun. SiliaFlash® P60 40-63 μm (230-400 mesh) was used for flash column chromatography. NMR spectra were recorded with an Agilent DD2™ 500 MHz spectrometer and calibrated using residual undeuterated solvent (chloroform-d: $^1H$ δ-1 6=7.26 ppm, $^{13}C$ δ=77.16 ppm) as an internal reference. Coupling constants (J) are reported in Hertz (Hz), and the following abbreviations were used to designate multiplicities: s=singlet, d=doublet, t=triplet, q=quartet, p=quintet, m=multiplet, br=broad. Infrared spectra were recorded using an ABB Bomem™ MB-Series Arid Zone™

FT-IR MB-155 Spectrometer. The absorptions are given in wavenumbers (cm$^{-1}$). High-resolution mass spectra (HRMS) were measured with an Agilent 6210 LC™ Time of Flight mass spectrometer in electrospray mode. Either protonated molecular ions [M+nH]n$^+$, sodium adducts [M+Na]$^+$ or ammonium adducts [M+NH$_4$]$^+$ were used for empirical formula confirmation. Optical rotations were measured with a JASCO DIP-360 digital polarimeter and are reported in units of 10$^1$ (deg cm$^2$ g$^{-1}$).

1,6:3,4-Dianhydro-β-D-galactopyranose (3). To a stirred solution of compound 2 (525 mg, 1.658 mmol) in methanol (16 mL) was added sodium methoxide (NaOMe) (90 mg, 1.658 mmol, 1 equiv). The mixture was stirred at room temperature for 2 h and then neutralized to pH 7 with Amberlyst® 15 acidic resin. The mixture was filtered and concentrated under reduced pressure to provide 3 as a white amorphous solid (239 mg, 1.658 mmol, quantitative yield).

1,6-Anhydro-3-azido-3-deoxy-β-D-galactopyranose (5). From compound 3: To a stirred solution of 3 (26 mg, 0.183 mmol) in dry DMF (3.6 mL) was added sodium hydride (60% dispersion in oil; 15 mg, 0.366 mmol, 2 equiv) under an argon atmosphere. The reaction mixture was stirred for 6 h and NaN$_3$ (60 mg, 0.916 mmol, 5 equiv) was added, followed by NH$_4$Cl (107 mg, 1.832 mmol, 10 equiv). The mixture was heated at 100° C. for 36 h and then cooled to room temperature. Silica gel (250 mg) was added and the mixture was concentrated under reduced pressure. The resulting dry-pack was purified by flash column chromatography (silica gel, MeOH/CH$_2$Cl$_2$, 0:100 to 3:17), providing an inseparable mixture of compounds 5 and 6 (9:1) as a white amorphous solid (31 mg, 0.165 mmol, 90% yield). From compound 2: To a stirred solution of compound 2 (1.658 g, 5.241 mmol) was added a 1 M aqueous solution of sodium hydroxide (52 mL). The mixture was stirred at room temperature for 6 h and then neutralized to pH ≈7 with Amberlyst® 15 acidic resin. The mixture was filtered and the residue rinsed with methanol (30 mL). The resulting filtrate was concentrated under reduced pressure to remove the methanol and transferred in a round bottom flask. Sodium azide (1.703 g, 26.203 mmol, 5 equiv) and NH$_4$Cl (2.803 g, 52.406 mmol, 10 equiv.) were added and the reaction mixture was heated under reflux for 2 days. After this time, more NaN$_3$ (681.4 mg, 10.481 mmol, 2 equiv) was added and the mixture was stirred 2 more days. The reaction was cooled down to room temperature and silica gel (10 g) was added. The mixture was concentrated under reduced pressure and the resulting dry-pack was purified by flash column chromatography (silica gel, MeOH/CH$_2$Cl$_2$, 0:100 to 3:17) to give a mixture of compounds 5 and 6 (4:1) as a white amorphous solid (775 mg, 4.14 mmol, 79% yield).

1,2,4,6-Tetra-O-acetyl-3-azido-3-deoxy-α/β-D-galactopyranose (7). To a stirred solution of a mixture of 5 and 6 (4:1; 728 mg, 3.887 mmol) in acetic anhydride (19 mL) at 0° C. was added three drops of triethylsilyl trifluoromethanesulfonate (≈40-60 μL, catalytic). After 30 min, a saturated aqueous NaHCO$_3$ solution (70 mL) was added and the mixture was stirred for 30 minutes. The reaction was extracted with CH$_2$Cl$_2$ (3×40 mL) and the combined organic phases were washed with a saturated aqueous NaHCO$_3$ solution (2×60 mL). The organic phase was dried over MgSO$_4$, filtered, and concentrated under reduced pressure. The crude oil was purified by flash column chromatography (silica gel, EtOAc/hexanes, 1:9 to 1:1) affording in 96% yield a mixture of compound 7 (α/β 6.5:1) as a white amorphous solid (1.114 g, 2.984 mmol) and compound 8 (α/β 6.5:1) as a colorless oil (280.2 mg, 0.751 mmol).

2,4,6-Tri-O-acetyl-3-azido-α-D-galactopyranosyl bromide (9). To a stirred solution of compound 7 (41 mg, 0.111 mmol) in dry CH$_2$Cl$_2$/EtOAc (2.2 mL, 10:1) was added TiBr$_4$ (82 mg, 0.222 mmol, 2 equiv) under an argon atmosphere. The reaction mixture was stirred at room temperature for 36 h and NaOAc (68 mg, 0.832 mmol, 7.5 equiv) was added. The mixture was washed with water (3×5 mL) and the organic layer was dried over Na$_2$SO$_4$, filtered, and concentrated under reduced pressure. The crude oil was purified by flash column chromatography (silica gel, EtOAc/hexanes, 3:7 to 1:1) providing 9 as a clear oil (34 mg, 0.087 mmol, 74% yield).

Tri-isopropylsilyl 2,4,6-tri-O-acetyl-3-azido-1-thio-β-D-galactopyranoside (10). A solution of compound 9 (344 mg, 0.866 mmol) in dry acetonitrile (17 mL) was purged with argon for 10 minutes, then K$_2$CO$_3$ (363 mg, 2.625 mmol, 3 equiv) was added, followed by TIPS-SH (376 μL, 1.750 mmol, 2 equiv). The mixture was stirred for 3 h at room temperature and concentrated under reduced pressure. The residue was dissolved in CH$_2$Cl$_2$ (40 mL), washed with water (2×20 mL), dried over Na$_2$SO$_4$, filtered, and concentrated under reduced pressure. The crude solid was purified by flash column chromatography (silica gel, EtOAc/hexanes, 1:9 to 2:3) providing compound 10 as an amorphous yellowish solid (359 mg, 0.657 mmol, 76% yield).

Bis-(2,4,6-tri-O-acetyl-3-azido-β-D-galactopyranosyl)-sulfane (11). To a solution of the tri-isopropylsilyl compound 10 (209 mg, 0.383 mmol) in dry acetonitrile (4 mL) was added bromide 9 (166 mg, 0.421 mmol, 1.1 equiv) in dry acetonitrile (4 mL). Argon was purged for 10 min through the solution and TBAF 1 M in THF (574 μL, 0.574 mmol, 1.5 equiv) was added. After 15 minutes, the mixture was concentrated under reduced pressure and the crude solid was purified by flash column chromatography (silica gel, EtOAc/hexanes, 3:7 to 1:1) providing compound 11 as an amorphous yellowish solid (187 mg, 0.283 mmol, 74% yield).

TD139 (GB0139; 1). To a solution of compound 11 (49 mg, 0.074 mmol) and CuI (7 mg, 0.037 mmol, 0.5 equiv) in DMF (3 mL) was added 1-ethynyl-3-fluorobenzene (34.2 μL, 0.296 mmol, 4 equiv) and DIPEA (25.8 μL, 0.148 mmol, 2 equiv). The mixture was stirred for 24 h at 50° C. and a saturated aqueous NH$_4$Cl solution (3 mL) was added. The organic solution was concentrated under reduced pressure and the residue was diluted with water (15 mL). The mixture was extracted with EtOAc (2×15 mL), and the combined organic phases were dried over Na$_2$SO$_4$, filtered, and concentrated under reduced pressure. The obtained crude was dissolved in MeOH (3 mL) and CH$_2$Cl$_2$ (1 mL). A solution of NaOMe (1 M in MeOH, 1 mL) was added and the resulting solution was stirred overnight at room temperature. The mixture was neutralized to pH 7 with Amberlyst® 15 acidic resin and the mixture was filtered and concentrated under reduced pressure. The resulting crude was purified by flash column chromatography (silica gel, CH$_2$Cl$_2$:MeOH 19:1→17:3) providing TD139 (1) as an amorphous white solid (31 mg, 0.048 mmol, 65% yield).

Results

The synthesis of TD139 (GB0139), summarized in Scheme 1a, was initiated with known 1,6-anhydro-4-O-p-tolylsulfonyl-β-D-glucopyranose 2. The formation of an epoxide led to 1,6:3,4-dianhydro-β-D-galactopyranose 3 in quantitative yield. The latter compound was treated with sodium hydride inducing a Payne rearrangement, allowing an equilibrium between 3 and 4. The opening of the epoxide with sodium azide yielded an inseparable mixture of 1,6-anhydro-3-azido-3-deoxy-β-D-galactopyranose 5 and 1,6- anhydro-4-azido-4-deoxy-β-D-glucopyranose 6 (5:6, 9:1) in 90% yield. Alternatively, compound 2 was treated with sodium hydroxide, promoting epoxide formation and Payne rearrangement. Then, the crude mixture was subjected to sodium azide, providing compounds 5 and 6 in 81% yield (5:6, 4:1).

The acetolysis of compounds 5 and 6 under acidic conditions (TESOTf, Ac$_2$O) furnished a separable mixture of known 3-azido-galactose 7 and 4-azido-glucose 8 in 96% yield. At this point, a strategy similar to that of the group of Nilsson was employed for the preparation of compound 1. Briefly, the α-galactosyl bromide 9 was slowly generated in 74% yield using TiBr$_4$ from intermediate 7. Then, a base promoted S$_N$2 substitution of galactosyl bromide 9 with TIPS-SH afforded tri-isopropylsilyl thio-galactoside 10 in 76% yield. The dimeric nature of the thiodigalactoside core was achieved by treating compounds 9 and 10 under tetra-butylammonium fluoride (TBAF) to generate bis-(2,4,6-tri-O-acetyl-3-azido-3-deoxy-β-D-galactopyranosyl)-sulfane 11 in 75% yield. Finally, triazole installation with a known alkyne preceded global deprotection, allowing the preparation of TD139 (GB0139) 1 in 2 steps and with a yield of 65%.

Example 2: Synthesis of Phenyl 2,4-di-O-benzyl-3-deoxy-3-[4-(3,4,5-trifluorophenyl)-1H–1,2,3-triazol-1-yl]-1-thio-α-D-galactopyranoside (24)

As a demonstration of the usefulness of levoglucosan as starting material for the construction of a specific galectin inhibitor,[16] the synthesis of monosaccharide derivatives similar to those developed by the group of Nilsson[17] was performed. Galectins are implicated both in intra- and extra-cellular activities and some monosaccharide derivatives are known to have good intracellular activity.[18]

A summary of the synthesis is depicted in Scheme 3. 1,6-anhydro-3-azido-3-deoxy-β-D-galactopyranose 5 was protected as benzyl ethers affording intermediate 22 in 91% yield. Then, compound 22 was subjected to a mixture of ZnI$_2$ and phenylthiotrimethylsilane in CH$_2$Cl$_2$ leading to phenyl thio-α-galactoside 23 in 79% yield. Finally, triazole installation with a known alkyne furnished the desired protected galectin inhibitor 24. Deprotection using standard techniques can be used to obtain the final galectin inhibitor.

(Synthesis of compound 24 from 1,6-anhydro-3-azido-3-deoxy-β-D-galactopyranose 5.

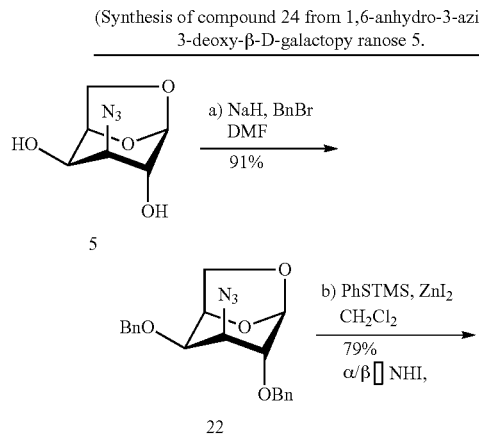

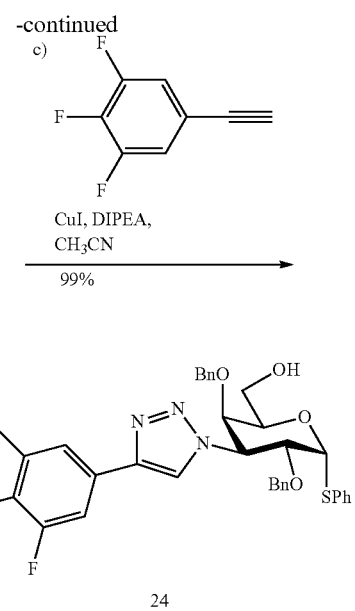

Reagents and conditions: a) BnBr (3 equiv), NaH (3 equiv), DMF, 0° C. to 23° C., 4 h, 91%; b) PhTMS (3 equiv), ZnI$_2$ (3 equiv), CH$_2$Cl$_2$, 23° C., 18 h, 79% (α/β = 20:1); c) 1-ethynyl-3,4,5-trifluorobenzene (3 equiv), CuI (0.5 equiv), DIPEA (3 equiv), 60° C., 19 h, 99% BnBr = benzyl bromide; DIPEA = N,N-diisopropylethylamine; PhTMS = phenylthiotrimethylsilane)

1,6-Anhydro-3-azido-2,4-di-O-benzyl-3-deoxy-β-D-galactopyranose (22): To a solution of 1,6-anhydro-3-azido-3-deoxy-β-D-galactopyranose 5 (84 mg, 0.449 mmol) in dry DMF (4.5 mL) at 0° C. was added sodium hydride (60% dispersion in oil) (53.9 mg, 1.347 mmol, 3 equiv) and benzyl bromide (160 μL, 1.347 mmol, 3 equiv). The reaction was allowed to go back to room temperature and was stirred for 4 h. The mixture was quenched by the addition of water (30 mL) and extracted with CH$_2$Cl$_2$ (2×20 mL). The organic phase was washed with water (20 mL), an aqueous 1 M solution of HCl (20 mL), and brine (20 mL). The organic phase was dried over Na$_2$SO$_4$, filtered, and concentrated under reduce pressure. The crude oil was purified by flash column chromatography (EtOAc/hexanes, 1:9 to 1:4) to afford 22 (150.8 mg, 0.408 mmol, 91% yield) as a colorless oil; $^1$H NMR (500 MHz, chloroform-d) δ 7.39-7.30 (m, 10H, OBn-2, OBn-4), 5.31 (t, $^3J_{H1-H2}=^4J_{H1-H3}=1.5$ Hz, 1H, H–1), 4.69 (d, J=11.9 Hz, 1H, OBn-4), 4.63 (d, J=8.7 Hz, 1H, OBn-2), 4.61 (d, J=8.6 Hz, 1H, OBn-2), 4.58 (d, J=12.1 Hz, 1H, OBn-4), 4.42 (tt, $^3J_{H5-H6b}=4.9$ Hz, $^4J_{H5-H4}=3.9$ Hz, $^4J_{H5-H3}=1.5$ Hz, $^3J_{H5-H6}=0.8$ Hz, 1H, H–5), 4.39 (dd, $^2J_{H6a-H6b}=7.3$ Hz, $^3J_{H6a-H5}=0.8$ Hz, 1H, H–6a), 4.01 (ddd, $^3J_{H4-H3}=5.1$ Hz, $^3J_{H4-H5}=3.8$ Hz, $^3J_{H4-H6b}=1.0$ Hz, 1H, H–4), 3.92 (dq, $^3J_{H3-H4}=5.5$ Hz, $^4J_{H3-H5}=^3J_{H3-H2}=^4J_{H3-H1}=1.4$ Hz, 1H, H–3), 3.61 (ddd, $^2J_{H6b-H6a}=7.5$ Hz, $^3J_{H6b-H5}=5.0$ Hz, $^3J_{H6b-H4}1.1$ Hz, 1H, H–6b), 3.49 (t, $^3J_{H2-H1}=^3J_{H2-H3}=1.7$ Hz, 1H, H–2); $^{13}$C NMR (126 MHz, chloroform-d) δ 137.5, 137.2, 128.81, 128.77, 128.44, 128.35, 128.2, 127.9 (m, 12C, OBn-2, OBn-4), 99.9 (s, 1C, C–1), 77.5 (s, 1C, C–2), 72.8 (s, 1C, OBn-2), 72.6 (s, 1C, C–4), 72.5 (s, 1C, C–5), 72.1 (s, 1C, OBn-4), 64.0 (s, 1C, C–6), 59.2 (s, 1C, C–2); HRMS calculated for C$_{20}$H$_{25}$O$_4^+$ [M+NH$_4$]$^+$385.1870, found 385.1881.

Phenyl 3-azido-2,4-di-O-benzyl-3-deoxy-1-thio-α-D-galactopyranoside (23): To a stirred solution of 22 (75.4 mg, 0.205 mmol) in CH$_2$Cl$_2$ (4 mL) was added phenylthioltrimethylsilane (117 μL, 0.616 mmol, 3 equiv) and zinc iodide (196.5 mg, 0.616 mmol, 3 equiv). The resulting suspension was stirred at room temperature for 18 h. The mixture was filtered over a Celite™ pad and concentrated under reduce pressure. The resulting crude product was dissolved in THF (2 mL) and a 1 M solution of tetrabutylammonium fluoride in THF was added dropwise (308 µL, 0.308 mmol, 1.5 equiv). After 15 minutes, the mixture was concentrated under reduced pressure and the crude residue was purified over flash column chromatography (EtOAc/hexanes, 1:5 to 1:1) to afford 23 (β/β, 20>1) as a white amorphous solid (77.4 mg, 0.162 mmol, 79% yield); $^1$H NMR (500 MHz, chloroform-d) δ 7.56-7.27 (m, 15H, OBn-2, OBn-4, SPh), 5.74 (d, $^3J_{H1-H2}$=5.4 Hz, 1H, H-1α), 4.91 (d, J=11.4 Hz, 1H, OBn-4), 4.79 (d, J=11.3 Hz, 1H, OBn-2), 4.70 (d, J=11.2 Hz, 1H, OBn-2), 4.60 (d, J=11.3 Hz, 1H, OBn-4), 4.32 (dd, $^3J_{H2-H3}$=9.9 Hz, $^3J_{H2-H1}$=5.3 Hz, 1H, H-2α), 4.27 (ddd, $^3J_{H5-H6b}$=6.6 Hz, $^3J_{H5-H6a}$=5.2 Hz, $^3J_{H5-H4}$=1.2 Hz, 1H, H-5α), 3.85 (dd, $^3J_{H4-H3}$=2.9 Hz, $^3J_{H4-H5}$=1.2 Hz, 1H, H-4α), 3.83 (dd, $^3J_{H3-H2}$=10.1 Hz, $^3J_{H3-H4}$=3.0 Hz, 1H, H-3α), 3.63 (dd, $^2J_{H6b-H6a}$=11.4 Hz, $^3J_{H6b-H5}$=6.9 Hz, 1H, H-6bα), 3.44 (dd, $^2J_{H6a-H6b}$=11.4 Hz, $^3J_{H6a-H5}$=5.2 Hz, 1H, H-6aα); $^{13}$C NMR (126 MHz, chloroform-d) δ 137.4, 137.1, 132.2, 129.1, 128.7, 128.6, 128.5, 128.32, 128.29, 128.2, 127.5 (m, 18C, OBn-2, OBn-4, SPh), 86.5 (s, 1C, C-1α), 75.22, 75.20, 75.15 (m, 3C, C-2, C-4, OBn-4), 72.3 (s, 1C, OBn-2), 71.2 (s, 1C, C-5), 62.2 (s, 1C, C-3), 61.9 (s, 1C, C-6); HRMS calculated for $C_{26}H_{28}O_4SN_3^+$ [M+H]$^+$ 478.1795, found 478.1801.

Phenyl 2,4-di-O-benzyl-3-deoxy-3-[4-(3,4,5-trifluorophenyl)-1H-1,2,3-triazol-1-yl]-1-thio-α-D-galactopyranoside (24): To a solution of compound 23 (34.5 mg, 0.072 mmol) and CuI (7 mg, 0.036 mmol, 0.5 equiv) in CH$_3$CN (1.5 mL) was added 1-ethynyl-3,4,5-trifluorobenzene (26.8 µL, 0.217 mmol, 3 equiv) and DIPEA (37.8 µL, 0.217 mmol, 3 equiv). The mixture was stirred 19 h at 60° C. before quenching with a saturated aqueous NH$_4$Cl solution (3 mL) followed by evaporation of the solvent under reduced pressure. The residue was diluted in water (15 mL) and extracted with CH$_2$Cl$_2$ (2×15 mL). The organic layer was washed with an aqueous 1 M solution of HCl (20 mL) and brine (20 mL). The organic phase was dried over Na$_2$SO$_4$, filtered, and concentrated under reduced pressure. The product was purified with a flash column chromatography (EtOAc/CH$_3$Cl, 1:19 to 2:5) to give 6 (45.5 mg, 0.072 mmol, 99% yield) as a yellowish amorphous solid. $^1$H NMR (500 MHz, chloroform-d) δ 7.59-6.98 (m, 17H, OBn-2, OBn-4, SPh, trifluoroaryl), 6.01 (d, $^3J_{H1-H2}$=5.3 Hz, 1H, H-1α), 5.22 (dd, $^3J_{H3-H2}$=11.3 Hz, $^3J_{H3-H4}$=3.1 Hz, 1H, H-3α), 4.71 (d, J=12.0 Hz, 1H, OBn-2), 4.59 (dd, $^3J_{H5-H1}$=11.1 Hz, $^3J_{H2-H3}$=5.2 Hz, 1H, H-2α), 4.58 (td, $^3J_{H5-H6b}$=6.8 Hz, $^3J_{H5-H6a}$=5.9 Hz, $^3J_{H5-H4}$=1.3 Hz, 1H, H-5α), 4.43 (d, J=12.0 Hz, 1H, OBn-2), 4.19 (d, J=11.1 Hz, 1H, OBn-4), 4.13 (dd, $^3J_{H4-H3}$=3.3 Hz, $^3J_{H4-H5}$=1.2 Hz, 1H, H-4α), 3.83 (d, J=11.1 Hz, 1H OBn-4), 3.77 (dd, $^3J_{H6b-H6a}$=11.2 Hz, $^3J_{H6b-H5}$=6.9 Hz, 1H, H-6bα), 3.64 (dd, $^3J_{H6a-H6b}$=11.2 Hz, $^3J_{H6a-H5}$=5.8 Hz, 1H, H-6aα); $^{13}$C NMR (126 MHz, chloroform-d) δ 136.5, 136.2, 132.7, 129.4, 128.79, 128.75, 128.74, 128.68, 128.6, 128.5, 128.0, 119.9, 109.8 (m, 26C, OBn-2, OBn-4, SPh, triazol, fluoroaryl), 86.1 (s, 1C, C-1α), 77.0 (s, 1C, C-4), 75.5 (s, 1C, OBn-4), 71.40, 71.36, 71.3 (m, 3C, OBn-2, C-2, C-5), 61.9 (s, 1C, C-3), 61.6 (s, 1C, C-6); $^{19}$F NMR (470 MHz, chloroform-d) δ −134.0 (dd, J=22.1, 8.6 Hz, 1F, F-4aryl), −160.9 (tt, J=20.1, 6.0 Hz, 2F, F-3,5aryl); HRMS calculated for $C_{34}H_{31}O_4SN_3F_3^+$ [M+H]$^+$ 634.1982, found 634.1998.

REFERENCES 1. a) Barondes, S. H.; Gastronovo, V.; Cooper, D. N. W.; Cummings, R. D.; Drickamer, K.; Feizi, T.; Gitt, M. A.; Hirabayashi, J.; Hughes, C.; Kasai, K.-I.; Leffler, H.; Liu, F.-T.; Lotan, R.; Mercurio, A. M.; Monsigny, M.; Pillai, S.; Poirier, F.; Raz, A.; Rigby, P. W. J.; Rini, J. M.; Wang, J. L. Cell 1944, 76, 597-598; b) Barondes, S. H.; Cooper, D. N. W.; Gitt, M. A.; Leffler, H. J. Biol. Chem. 1994, 269, 20807-20810.
2. a) Rabinovich, G. A.; Toscano, M.; Jackson, D. A.; Vasta, G. Curr. Opin. Struct. Biol. 2007, 17, 513-520; b) Liu, F.-T.; Rabinovich, G. A. Nat. Rev. Cancer 2005, 5, 29-41; c) Califice, S.; Castronovo, V.; van den Bride, F. Int. J. Oncol. 2004, 25, 983-992.
3. Denavit, V.; Lainé, D.; Temblay, T.; St-Gelais, J.; Giguère, D. Trends Glycosc. Glycotechnol. 2018, 30, SE21-SE40.
4. Girard, A.; Magnani, J. L. Trends Glycosc. Glycotechnol. 2018, 30, SE211 SE220.
5. Delaine, T.; Collins, P.; MacKinnon, A.; Sharma, G.; Stegmayr, J.; Rajput, V.; Mandal, S.; Cumpstey, I.; Larumbe, A.; Salameh, B. A.; Kahl-Knutsson, B.; van Hattum, H.; van Scherpenzeel, M.; Pieters, R. J.; Sethi, T.; Schambye, H.; Oredsson, S.; Leffler, H.; Blanchard, H.; Nilsson, U. J. ChemBioChem 2016, 17, 1759-1770.
6. Nilsson, U. J.; Leffler, H.; Henderson, N.; Sethi, T.; Mackinnon, A. (2014) WO2014067986A1.
7. Lowary, T. L.; Hindsgaul, 0. Carbohydr. Res. 1994, 251, 33-67.
8. Hoffmann-Roder, A.; Johannes, M. Chem. Commun. 2011, 47, 9903-9905.
9. Oberg, C. T.; Noresson, A.-L.; Delaine, T.; Larumbe, A.; Tejler, J.; von Wachenfeldt, H.; Nilsson, U. J. Carbohydr. Res. 2009, 344, 1282-1284.
10. Peterson, K.; Wymouth-Wilson, A.; Nilsson, U. J. J. Carbohydr. Chem. 2015, 34, 490-499.
11. Grindley, B. T.; Thangarasa, R. Carbohydr. Res. 1988, 172, 311-318.
12. Cerny, M.; Buban, I.; Pacak, J. Collect. Czech. Chem. Commun. 1963, 28, 1569-1578.
13. Mubarak, A.; Fraser-Reid, B. J. Org. Chem. 1982, 47, 4265-4268.
14. Peterson, K.; Kumar, R.; Stenstrom, 0.; Verma, P.; Verma, P. R.; Hakansson, M.; Kahl-Knutsson, B.; Zetterberg, F.; Leffler, H.; Akke, M.; Logan, D. T.; Nilsson, U. J. J. Med. Chem. 2018, 61, 1164-1175.
15. Mandal, S.; Nilsson, U. J. Org. Biomol. Chem. 2014, 12, 4816-4819.
16. St-Gelais, J.; Denavit, V.; Giguere, D. Org. Biomol. Chem. 2020, 18, 3903-3907.
17. Zetterberg, F. R.; Peterson, K.; Johnsson, R. E.; Brimert, T.; Hakansson, M.; Logan, D. T.; Leffler, H.; Nilsson, U. J. ChemMedChem 2018, 13, 133-137; b) Zetterberg, F.; Nilsson, U. J.; Brimert, T.; Peterson, K.; Jansson, K. WO2020078808; c) Zetterberg, F.; Nilsson, U. J. WO 2020078807; d) Zetterberg, F. WO2019137971; e) Jalagam, P. R.; Nair, S. K.; Panda, M.; Regueiro-Ren, A. WO2019075045; f) Zetterberg, F.; Nilsson, U. J.; Leffler, H. WO2018011094; g) Zetterberg, F.; Leffler, H.; Nilsson, U. J. WO2018011093; h) Brimert, T.; Johnsson, R.; Leffler, H.; Nilsson, U. J.; Zetterberg, F. WO2016120403.
18. Stegmayr, J.; Zetterberg, F.; Carlsson, M. C.; Huang, X.; Sharma, G.; Kahl-Knutson, B.; Schambye, H.; Nilsson, U. J.; Oredsson, S.; Leffler, H. Sci. Rep. 2019, 9, 2186.

All publications, patents, and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:
1. A method for synthesizing a 3-azido-3-deoxy-D-galactopyranose of formula IV

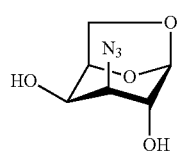

said method comprising:
(a) epoxidation of a compound of formula II to form a compound of formula III

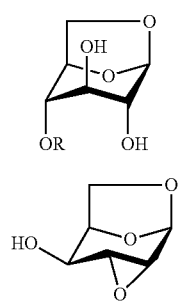

where R is an activating group; and
(b) ring opening of the epoxide of the compound of formula III with an inorganic or organic azide to produce the compound of formula IV;
wherein the activating group is a sulfonyl, trifluoromethanesulfonyl, or imidazole-1- sulfonyl.

2. The method of claim 1, wherein, prior to step (a), the method additionally comprises treating levoglucosan with an activating agent to produce the compound of formula II.

3. The method of claim 1, wherein during the epoxidation step the epoxide is introduced by a two-step reaction or a single step reaction.

4. The method of claim 3, wherein the two-step reaction comprises epoxidation by treatment of the compound of formula II followed by treatment with a base.

5. The method of claim 3, wherein the single step reaction comprises treatment of the compound of formula II with a base.

6. A method for synthesis of a compound having the structure of formula Ia or Ib,

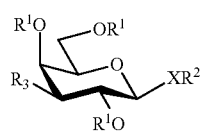

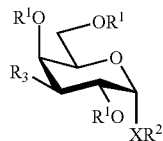

wherein:
each $R^1$ is independently H or a protecting group;
$R^2$ is alkyl, substituted alkyl, aryl, substituted aryl, heteroaryl, substituted heteroaryl, or a substituted α- or β-D-galactopyranosyl;
$R^3$ is a substituted or unsubstituted nitrogen-containing functional group; and
X is O, S, or N,
said method comprising:
(a) epoxidation of a compound of formula II to form a compound of formula III

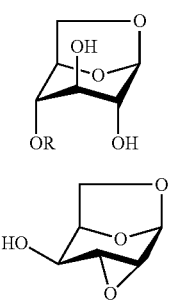

where R is an activating group;
(b) ring opening the epoxide of the compound of formula III with an inorganic or organic azide to produce the compound of formula IV

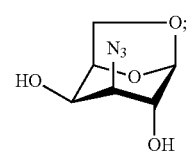

(c) protecting the alcohol groups of the compound of formula IV and subsequently treating the protected compound with an activator to break the 1,6-anhydro bridge, or treating the compound of formula IV with an activator to break the 1,6-anhydro bridge and simultaneously protecting the alcohol groups;
(d) performing one or more nucleophilic substitutions to introduce $R^2X$ at C1 of the galactopyranose ring of the product of step (c), after or simultaneously with breaking the 1,6-anhydro bridge, to form a compound of formula Ia' or Ib'

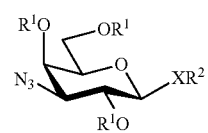

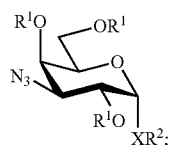

and, optionally (e) treating the compound of formula Ia' or Ib' to replace the azide with another nitrogen-containing functional group;

wherein the activating group is a sulfonyl, trifluoromethanesulfonyl, or imidazole-1-sulfonyl.

7. The method of claim 6, additionally comprising, prior to step (e), performing a base-promoted substitution of a galactopyanosyl-1-halide with the compound formula Ia' to form a compound of Ia in which $R^2$ is a β-D-galactopyranosyl.

8. The method of claim 6, wherein step (e) comprises performing an azide-alkyne cycloadditon using an alkyne of formula VI

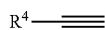

to produce the compound of formula Ia or Ib in which $R^3$ is an $R^4$-substituted triazole, wherein $R^4$ is a mono-, di- or tri-fluorophenyl.

9. The method of claim 6, wherein step (e) comprises reduction of the azide to produce an amino group at the C3 of the galactopyranose ring or rings.

10. The method of claim 9, wherein step (e) further comprises:

(i) an electrophilic addition at the amino group;

(ii) sulfonylation of the amino group;

(iii) reductive amination by treatment with sodium cyanoborohydride and an aldehyde;

(iv) treatment with an acyl chloride or carboxylic acid to produce an amide at the C3 of the galactopyranose ring;

(v) treatment with an aryl halide to produce an aniline at the C3 of the galactopyranose ring; or (vi) treatment with an epoxide to produce an alkanolamine at the C3 of the galactopyranose ring.

11. The method of claim 6, which additionally comprises deprotecting the alcohol groups after step (e).

12. The method of claim 6, wherein X is S.

13. The method of claim 6, wherein $R^3$ is 3,4,5-trifluorophenyl triazole.

14. The method of claim 6, wherein each $R^1$ is independently H or Bn, $R^2$ is phenyl, $R^3$ is 3,4,5-trifluorophenyl triazole and X is S.

15. The method of claim 6, wherein the compound of formula Ia or Ib is a galectin antagonist and the galectin antagonist is

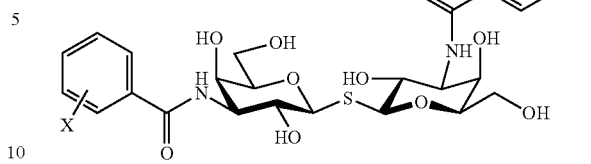

wherein each X is one or more halo group.

16. The method of claim 6, wherein the compound of formula Ia or Ib is a galectin antagonist selected from the group consisting of:

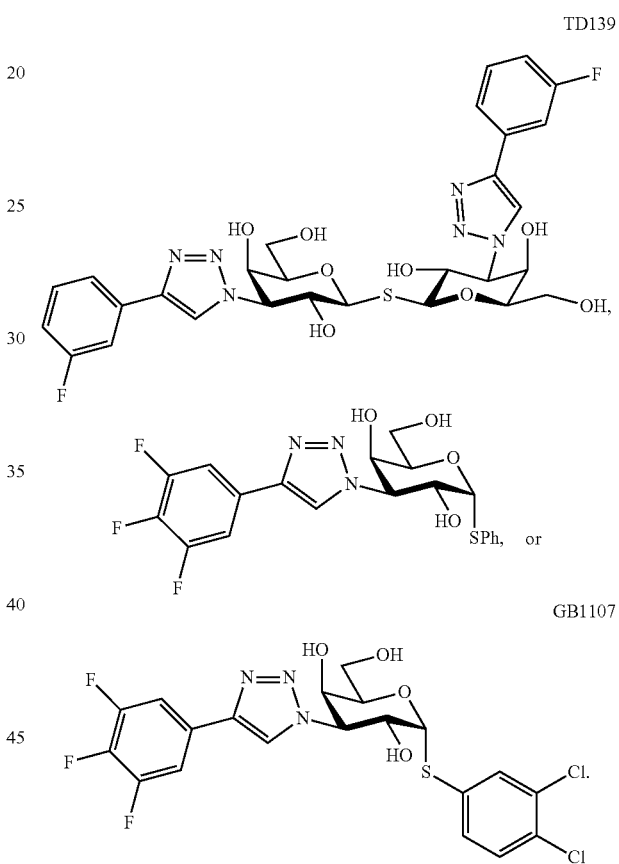

17. The method of claim 6, wherein the protecting group is selected from the group consisting of acetyl, benzyl (Bn), p-methoxybenzyl (PMB), substituted benzyl, trimethylsilyl (TMS), t-butyldimethylsilyl (TBS), and t-butyldiphenylsilyl (TBDPS).

18. The method of claim 6, wherein the nitrogen-containing functional group is selected from the group consisting of azide, amine, amide, sulfonamide, carbamate and substituted nitrogen-based heterocycle.

19. The method of claim 18, wherein the substituted nitrogen-based heterocycle is mono-fluorophenyl triazole, di-fluorophenyl triazole, or trifluorophenyl triazole.

* * * * *